United States Patent [19]

Martinez

[11] Patent Number: 4,577,629

[45] Date of Patent: Mar. 25, 1986

[54] SURGICAL CUTTING INSTRUMENT FOR OPHTHALMIC SURGERY

[75] Inventor: Miguel Martinez, Irvine, Calif.

[73] Assignee: CooperVision, Inc., Irvine, Calif.

[21] Appl. No.: 546,418

[22] Filed: Oct. 28, 1983

[51] Int. Cl.$^4$ ............................................. A61B 17/32
[52] U.S. Cl. ...................................... 128/305; 604/22
[58] Field of Search ........................... 128/305; 604/22

[56] References Cited

U.S. PATENT DOCUMENTS

| | | | |
|---|---|---|---|
| 3,776,238 | 12/1973 | Peyman et al. | 128/305 |
| 3,884,238 | 5/1975 | O'Malley et al. | 128/305 |
| 3,994,297 | 11/1976 | Kopf | 128/305 |
| 4,011,867 | 3/1977 | Seiler | 128/305 |
| 4,246,902 | 1/1981 | Martinez | 128/305 |
| 4,428,748 | 1/1984 | Peyman et al. | 128/305 X |

*Primary Examiner*—Hugh R. Chamblee
*Attorney, Agent, or Firm*—Epstein & Edell

[57] ABSTRACT

A surgical cutting instrument for use in ophthalmic surgery includes a cylindrical body having front and rear plugs in opposite ends thereof with a piston disposed in a centrally disposed chamber in the body, and a probe having an elongate tubular outer member with a proximal end received in an axial bore in the front plug and a closed distal end with a port therein and an elongate tubular inner member slidably disposed in the outer member with a distal end movable across the port to provide a cutting action and a portion fixed in an axial bore in the piston such that the probe inner member is moved with the piston, the rear plug having an axial bore therethrough aligned with the probe inner member to permit evacuation of cut material through the surgical cutting instrument and a second bore therethrough for supplying pressure to the chamber to move the piston against a spring bias. The surgical cutting instrument is designed to be economically disposable by being constructed of a minimal number of parts requiring minimal machining and tooling and capable of quick and simple assembly.

10 Claims, 5 Drawing Figures

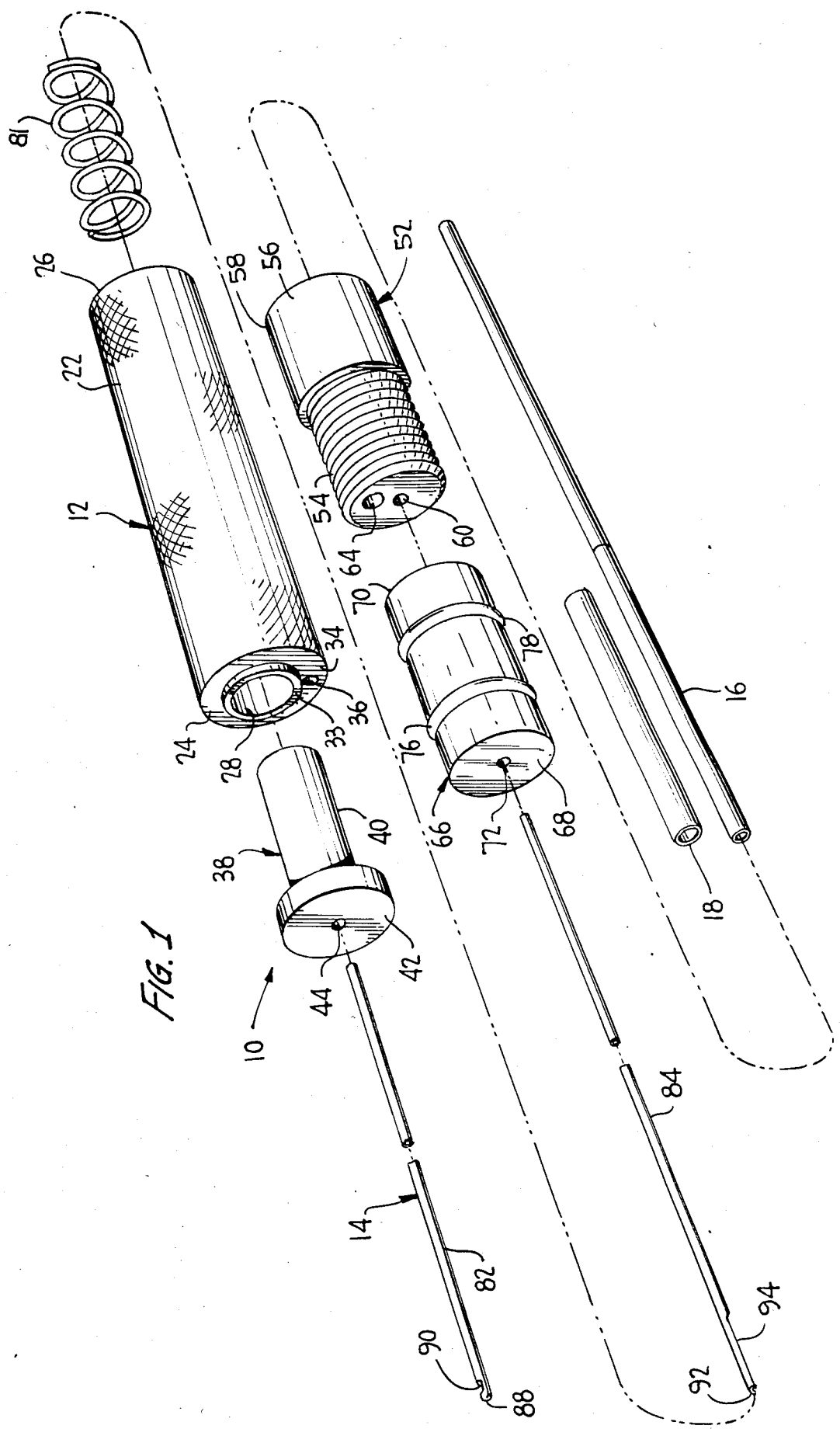

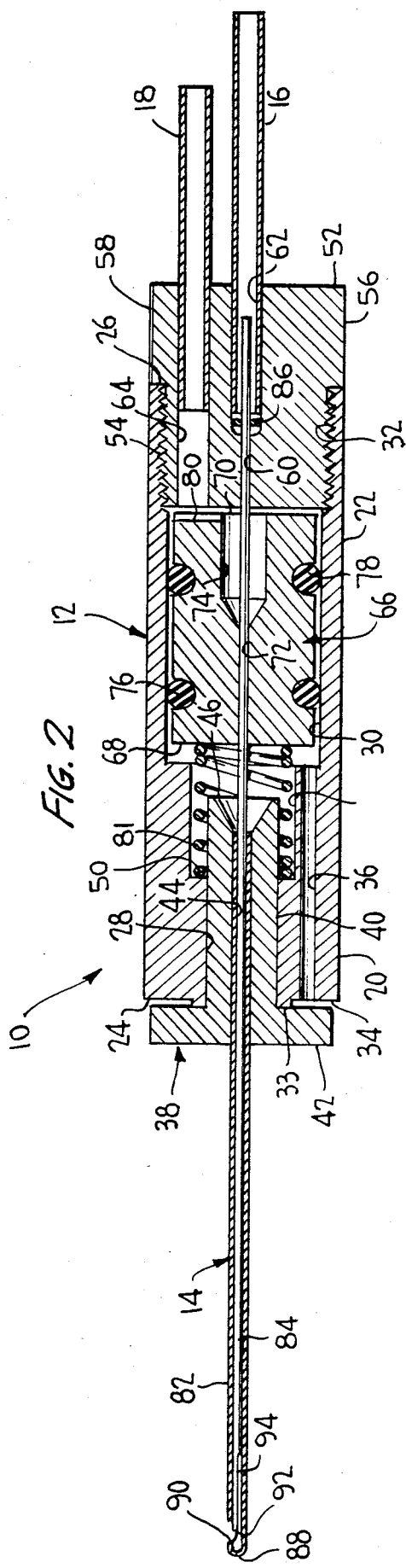
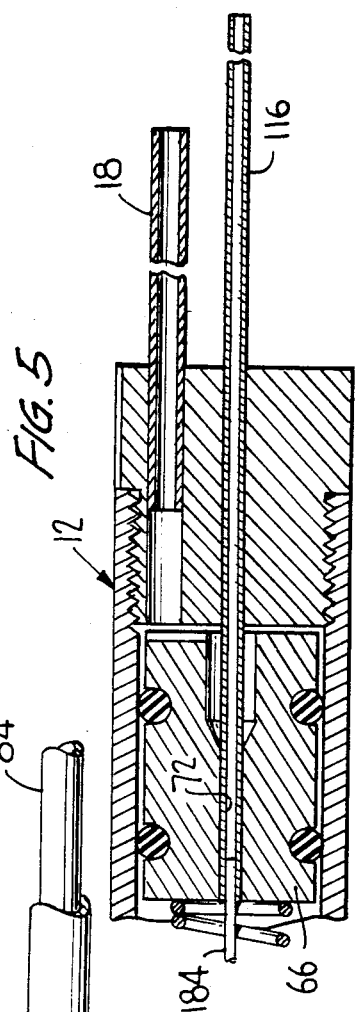
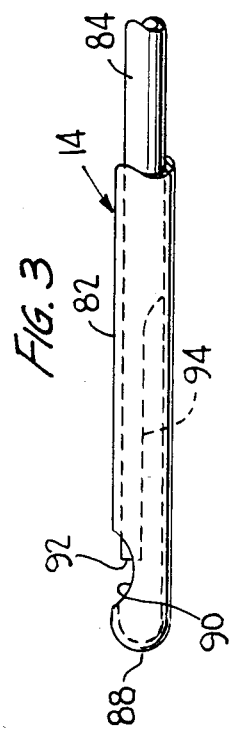
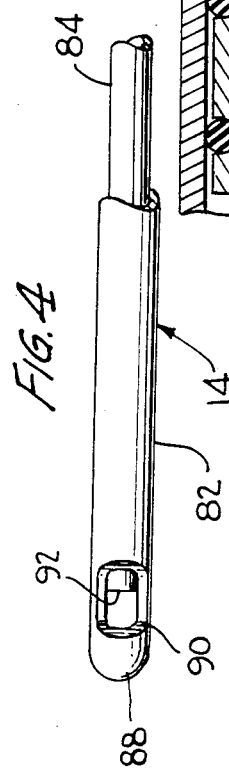

SURGICAL CUTTING INSTRUMENT FOR OPHTHALMIC SURGERY

BACKGROUND OF THE INVENTION

1. Field of the Invention

The present invention pertains to surgical cutting instruments for use in ophthalmic surgery and, more particularly, to such surgical cutting instruments designed to be economically disposable.

2. Discussion of the Prior Art

Many ophthalmic surgeons presently use surgical cutting instruments for cutting and removing vitreous, blood clots, cataracts, lenses and other matter from the eye. Such surgical cutting instruments use various means to cut or separate the matter from the eye including pulsating fluid jets or mechanical cutting or shearing mechanisms, such as rotating members or reciprocating members, the latter being exemplified by U.S. Pat. No. 3,776,238 to Peyman et al, U.S. Pat. No. 3,884,238 to O'Malley et al, U.S. Pat. No. 3,994,297 to Kopf, U.S. Pat. No. 4,011,869 to Seiler, Jr., U.S. Pat. No. 4,246,902 to Martinez and U.S. Pat. No. 4,314,560 to Helfgott et al. While such surgical cutting instruments have been well received and are commonly used in ophthalmic surgery, there is a need for an economically disposable surgical cutting instrument that can be available along with other instruments and materials required for surgery, particularly cataract surgery, in a sterilized package or kit. However, any economically disposable surgical cutting instrument must still provide precise cutting and adequate suction and evacuation of cut material and must be designed and shaped to facilitate manipulation by a surgeon. The above mentioned patents disclose surgical cutting instruments with a tubular outer member having a tubular inner member sliding therein and reciprocated by various means of motive power. These instruments have the disadvantages of not being economically disposable in that they include a number of intricate parts, require precision machining and tooling, and necessarily require complicated assembly procedures and of requiring disassembly for sharpening and sterilization.

SUMMARY OF THE INVENTION

Accordingly, it is a primary object of the present invention to provide an economically disposable surgical cutting instrument for use in ophthalmic surgery overcoming the above mentioned disadvantages of the prior art while providing precision cutting and sufficient evacuation of cut material.

Another object of the present invention is to construct a surgical cutting instrument of a minimal number of uncomplicated parts that can be inexpensively produced and assembled.

A further object of the present invention is to axially align an evacuating tube with an inner reciprocating cutting member of a surgical cutting instrument probe to permit axial passage of cut material from the probe through the surgical cutting instrument.

The present invention has a further object in that a rigid evacuating tube coupled with a rear plug of a surgical cutting instrument remains stationary while receiving cut material to be evacuated from a probe inner reciprocating cutting member aligned with the evacuating tube.

Yet another object of the present invention is to form a reciprocating probe surgical cutting instrument of a cylindrical body having front and rear plugs in opposite ends to mount the probe and evacuating and supply tubes and to house a piston driving the probe.

Some of the advantages of the present invention over the prior art are that assembly is facilitated by force fitting and axial alignment of parts, cost of parts and assembly is minimized and the surgical cutting instrument is small and light weight (about 4.6 grams) to be easily handled by a surgeon.

The present invention is generally characterized in a surgical cutting instrument useful in ophthalmic surgery including a cylindrical, hollow body having a front end, a rear end and a centrally disposed chamber therein; a front plug received in the front end of the body and having an axial bore therethrough; a piston disposed in the chamber to be movable in a reciprocating manner toward and away from the front end, the piston carrying sealing rings therearound and having a front end, a rear end and an axial bore therethrough with a widened portion adjacent the rear end of the piston; a spring disposed in the body engaging the front end of the piston to bias the piston away from the front end of the body; a probe including an elongate tubular outer member having a proximal end secured in the axial bore in the fron plug, a closed distal end, and a port adjacent the distal end, and an elongate tubular inner member slidably disposed in the outer member and having a portion fixed in the axial bore in the piston and a distal end movable across the port to provide a cutting action; a rear plug received in the rear end of the body and having an axial bore therethrough aligned with the probe inner member to permit passage of cut material through the surgical cutting instrument and a second bore therethrough communicating with the chamber for receiving pressure to move the piston and the probe inner member against the bias of the spring; and evacuating tube means communicating with the probe inner member and adapted to be connected with a source of suction to draw cut material through the probe inner member.

Other objects and advantages of the present invention will become apparent from the following description of the preferred embodiment taken in conjunction with the accompanying drawings.

BRIEF DESCRIPTION OF THE DRAWINGS

FIG. 1 is a longitudinal cross section of a surgical cutting instrument according to the present invention.

FIG. 2 is an exploded isometric view of the surgical cutting instrument of FIG. 1.

FIGS. 3 and 4 are broken side and top views, respectively, of the cutting tip of the surgical cutting instrument of FIG. 1.

FIG. 5 is a broken, longitudinal cross section of a modification of the surgical cutting instrument of the present invention.

DESCRIPTION OF THE PREFERRED EMBODIMENT

A surgical cutting instrument according to the present invention is shown in FIGS. 1 and 2 and includes a body 12 with a probe 14 extending from one end and an evacuating tube 16 and a pressure supply tube 18 extending from an opposite end of the body. The surgical cutting instrument 10 can be utilized with any suitable source of suction communicating with evacuating tube 16 and any suitable pulsed source of pressurized fluid, preferably air, communicating with supply tube 18. The surgical cutting instrument 10 is particularly adapted for use with the Ocutome Model 8000 manufactured by CooperVision Inc. which incorporates a source of suction and a pressure source capable of supplying pressure pulses at an adjustable frequency of up to four hundred pulses per minute or supplying a single pulse upon actuation of a switch to produce a single pulse and a corresponding single cutting stroke. The suction supplied to evacuating tube 16 is controlled in conventional manner by a foot or hand operated device coupled with the source of suction.

The body 12 is formed of a cylindrical barrel 20, preferably made of aluminum, having a knurled outer surface 22, the body having an outer diameter of about 0.4″ and a length from a front end 24 to a rear end 26 of about 1.3″ in order to be easily held and manipulated by a surgeon. The front end 24 has an axial bore 28 therein communicating with a chamber 30, and the rear end 26 has an axial, internally threaded bore 32 leading to chamber 30. An annular shoulder 33 is formed on the front end 24 to define an outer annular space 34 communicating with chamber 30 via a vent passage 36 extending parallel to the axis of the barrel.

A front plug 38, preferably made of plastic, has a stem 40 received in bore 28 with a force fit and a head 42 abutting shoulder 33, the front plug 38 having an axial bore 44 therethrough with a conical or tapered internal end 46 positioned in a reduced diameter pocket 48 extending from the distal end of chamber 30 and terminating at a shoulder 50. A rear plug 52 has an externally threaded stem 54 threadedly engaging the threaded bore 32 at the rear end of the body 12 and a head 54 abutting the rear end 26, the head 56 carrying an indexing groove 58 along its peripheral edge. An axial bore through the rear plug has a reduced diameter portion 60 adjacent chamber 30 leading to an increased diameter portion 62 receiving evacuating tube 16 with a force fit. An axially offset bore 64 passes through the rear plug to communicate with chamber 30, and supply tube 18 is force fit in bore 64. Rear plug 52 is preferably made of plastic while tubes 16 and 18 are preferably rigid and made of stainless steel.

A cylindrical piston 66, preferably made of plastic, is disposed in chamber 30 and has a length of about 0.470 inches, a front end 68 and a rear end 70 with an axial bore 72 extending therebetween, axial bore 72 having a widened portion 74 adjacent the rear end of the piston. The piston 66 carries a pair of axially spaced O-ring seals 76 and 78 engaging the wall of chamber 30, and a positioning slot 80 extends radially along rear end 70 of the piston between the widened bore portion 74 and the side wall of the piston. A helical spring 81 is mounted in compression between the front end 68 of the piston and shoulder 50 on the body to bias the piston toward rear plug 52.

The probe 14 is formed of an elongate, tubular outer member 82 preferably made of 20 gauge stainless steel with a length of 1.48 inches, and an elongate tubular inner member 84 prefereably made of 23 gauge stainless steel, having a length of 2.5 inches. The outer member 82 has a proximal end secured in bore 44 in front plug 38 with a force fit while the inner member 84 is secured in bore 72 in piston 66 with a force fit. Inner member 84 has a diameter to permit reciprocating sliding movement in outer member 82 and to produce a sliding fit in bore 60 in rear plug 52 to allow the tail of the inner member to reciprocate within the rear plug and within bore portion 62 and evacuating tube 16. The sliding fit of the inner member in the rear plug produces a seal when the plug is made of a resilient plastic; however, to improve the seal a flexible washer 86 could be carried on the inner member positioned in the increased diameter portion 62 of the axial bore through rear plug 52 between the end of evacuating tube 16 and the reduced diameter bore portion 60 or an 0-ring seal (not shown) could be mounted around inner member 84 adjacent reduced diameter bore portion 60. As best shown in FIGS. 3 and 4, the distal end 88 of outer probe member 82 is closed and has a rounded configuration, and a port 90 is cut in the side wall of the outer member adjacent distal end 88. The distal end 92 of inner member 84 is cut away at 94 to have a reduced cross section and provide shearing cutting action as it is moved across port 90 toward the closed end of the outer member.

As will be appreciated from the above, the surgical cutting instrument 10 is constructed of a minimal number of components and can be simply assembled by force fitting the outer probe member 82 in front plug 38, force fitting front plug 38 in the front end of body 12, force fitting inner probe member 84 in piston 66, placing spring 81 in pocket 48, inserting the inner probe member and the piston carrying the 0-ring seals in chamber 30 from the rear end of the body with inner member alignment with the outer member facilitated by taper 46, aligning the distal ends of the probe members by rotating piston 66 via a tool engaging positioning slot 80, force fitting evacuating tube 16 and supply tube 18 in rear plug 52, and screwing rear plug 52 into the rear end of the body 12 with inner probe member 84 aligned with bore 60, it being noted that widened bore portion 74 permits slight flexing of inner probe member 84 thereby facilitating assembly and reducing the precision alignment required for the axial bores through the piston and the rear plug.

In use, the surgical cutting instrument 10 will be coupled with a suitable controlled suction source via a length of flexible tubing connected with evacuating tube 16 and a suitable controllable pulsed pneumatic source via a length of flexible tubing connected with supply tube 18, such sources being available in the Ocutome Model 8000 manufactured by CooperVision, Inc. as mentioned above. The surgeon, in utilizing the surgical cutting instrument to remove material from the eye, adjusts the frequency of the pressure source as desired to control the frequency and number of cutting strokes of the probe.

With no pressure applied to supply tube 18, spring 81 biases piston 66 against rear plug 52 which moves the inner probe member away from the closed end of the outer probe member to move the distal end 92 thereof away from port 90. When a pressure pulse is supplied to supply tube 18, the force of spring 81 is overcome, and piston 66 is moved toward the front of body 12 until it contacts the end wall of chamber 30, air in the chamber being vented through passage 36 and expelled radially via space 34 away from the surgical site. Movement of piston 66 causes movement of inner probe member 84 to move distal end 92 across port 90 to cut or shear material extending into the port. Suction applied to the tip of the probe 14 via evacuating tube 16 and inner member 84 withdraws the cut material from the surgical cutting instrument and also echances cutting operation by drawing material to be cut into port 90 prior to the cutting stroke of the inner probe member 84. At the end of the pressure pulse, the removal of pressure from the rear end of the piston allows the spring 81 to force the piston back against the rear plug with air supplied to chamber 30 at the front end of the piston via space 34 and passage 36. Adjustment of the Ocutome Model 8000, permits the frequency and number of pressure pulses and, therefore, cutting strokes to be controlled and the application of suction can be controlled by the surgeon via a manually-operated device.

By providing a sliding fit between inner probe member 84 and bore 60 in rear plug 52 and by utilizing an evacuating tube having an inner diameter greater than the outer diameter of the inner probe member, reciprocating movement of the inner probe member is not transmitted to the evacuating tube which remains stationary during operation. The seal between the inner probe member and the rear plug prevents the pressurized air from the supply tube from reaching the open end of the inner probe member.

A modification of the surgical cutting instrument of the present invention is shown in FIG. 5 with parts identical to parts of the surgical cutting instrument of FIG. 1 being given identical reference numbers and similar parts being given reference numbers with 100 added. The primary difference between the modification of FIG. 4 and the surgical cutting instrument of FIG. 1 is that the evacuating tube 116 has an inner diameter substantially the same as the outer diameter of the inner probe member 184 and extends through axial bore 160 in rear plug 152 with a sliding fit and through axial bore 72 in piston 66 with a force fit to terminate adjacent the front end 68 while the inner probe member 184 extends only a short distance into evacuating tube 116 and is secured to the evacuating tube by any suitable means, such as solder or adhesive. Accordingly, reciprocating movement of the inner probe member results in reciprocating movement of the evacuating tube.

From the above, it will be appreciated that by providing axial flow for cut material, the structure and assembly of the surgical cutting instrument of the present invention is simplified to an extent to allow the surgical cutting instrument to be economically disposable thereby avoiding the problems associated with sterilization and sharpening.

Inasmuchas the present invention is subject to many variations, modifications and changes in detail, it is intended that all subject matter discussed above or shown in the accompanying drawings be interpreted as illustrative and not in a limiting sense.

What is claimed is:

1. A surgical cutting instrument useful in ophthalmic surgery comprising
   a cylindrical, hollow body having a front end, a rear end and a centrally disposed chamber therein;
   a front plug received in said front end of said body and having an axial bore therethrough;
   a piston disposed in said chamber to be movable in a reciprocating manner toward and away from said front end, said piston carrying sealing means therearound and having a front end, a rear end and an axial bore therethrough with a widened portion adjacent said rear end of said piston;
   spring means disposed in said body engaging said front end of said piston to bias said piston away from said front end of said body;
   probe means including an elongate tubular outer member having a proximal end secured in said axial bore in said front plug, a closed distal end, and a port adjacent said distal end, and an elongate tubular inner member slidably disposed in said outer member and having a portion fixed in said axial bore in said piston and a distal end movable across said port to provide a cutting action;
   a rear plug received in said rear end of said body and having an axial bore therethrough aligned with said probe inner member to permit passage of cut material through said surgical cutting instrument and a second bore therethrough communicating with said chamber for receiving pressure to move said piston and said probe inner member against the bias of said spring means; and
   evacuating tube means communicating with said probe inner member and adapted to be connected with a source of suction to draw cut material through said probe inner member.

2. A surgical cutting instrument as recited in claim 1 wherein said evacuating tube means includes a rigid tube extending through said rear plug axial bore with a sliding fit and secured in said piston axial bore and said portion of said probe inner member fixed in said piston axial bore is secured to said rigid tube.

3. A surgical cutting instrument as recited in claim 1 wherein said piston rear end has a positioning slot therein to facilitate rotational alignment of said piston during assembly of said surgical cutting instrument.

4. A surgical cutting instrument as recited in claim 1 wherein said probe inner member extends into a portion of said rear plug axial bore with a sliding fit whereby said evacuating tube means remains stationary while said probe inner member reciprocates with movement of said piston.

5. A surgical cutting instrument as recited in claim 4 wherein said rear plug axial bore includes an increased diameter portion receiving the end of said probe inner member and said evacuating tube means includes a rigid tube received in said increased diameter portion of said rear plug axial bore, said rigid tube having an inner diameter greater than the outer diameter of said probe inner member.

6. A surgical cutting instrument as recited in claim 5 and further comprising seal means disposed in said rear plug axial bore engaging said probe inner member.

7. A surgical cutting instrument as recited in claim 1 wherein said front end of said body has an annular shoulder thereon, said front plug has a stem received in said front end of said body and a radially extending head abutting said annular shoulder to define an annular space adjacent said front end of said body, and said body includes a vent passage communicating with said annular space and said chamber whereby air from said chamber is vented in a radial direction through said annular space.

8. A surgical cutting instrument as recited in claim 7 wherein said front plug stem has a tapered end to facilitate insertion of said probe inner member in said probe outer member.

9. A surgical cutting instrument as recited in claim 1 wherein said rear end of said body is internally threaded and said rear plug is externally threaded and threadedly engages said rear end of said body.

10. A surgical cutting instrument as recited in claim 9 and further comprising a rigid tube received in said second bore in said rear plug for supplying pressure to said chamber.

* * * * *